United States Patent
Irianni et al.

(10) Patent No.: US 9,427,446 B2
(45) Date of Patent: Aug. 30, 2016

(54) STABLE INJECTABLE COMPOSITION CONTAINING DICLOFENAC AND THIOCOLCHICOSIDE

(71) Applicant: EPIFARMA S.R.L., Episcopia (IT)

(72) Inventors: Giuseppe Irianni, Episcopia (IT); Cristina Macelloni, Rozzano (IT); Luca Teseschi, Cura Carpignano (IT)

(73) Assignee: EPIFARMA S.R.L., Episcopia (PZ) (IT)

( * ) Notice: Subject to any disclaimer, the term of this patent is extended or adjusted under 35 U.S.C. 154(b) by 0 days.

(21) Appl. No.: 14/432,115

(22) PCT Filed: Oct. 21, 2013

(86) PCT No.: PCT/EP2013/071925
§ 371 (c)(1),
(2) Date: Mar. 27, 2015

(87) PCT Pub. No.: WO2014/064030
PCT Pub. Date: May 1, 2014

(65) Prior Publication Data
US 2015/0238510 A1  Aug. 27, 2015

(30) Foreign Application Priority Data
Oct. 22, 2012 (IT) .............. MI2012A1782

(51) Int. Cl.
*A61K 31/704* (2006.01)
*A61K 31/196* (2006.01)
*A61K 9/08* (2006.01)
*A61K 9/00* (2006.01)

(52) U.S. Cl.
CPC ........... *A61K 31/704* (2013.01); *A61K 9/0019* (2013.01); *A61K 9/08* (2013.01); *A61K 31/196* (2013.01)

(58) Field of Classification Search
CPC ..................... A61K 31/704; A61K 31/196
See application file for complete search history.

(56) References Cited

U.S. PATENT DOCUMENTS 6,054,484 A * 4/2000 Sekine ................ A61K 9/0014
514/567

FOREIGN PATENT DOCUMENTS

| FR | 2735369 A1 | 1/1996 |
| WO | 9641635 | 12/1996 |
| WO | 2012053012 | 4/2012 |

OTHER PUBLICATIONS

EPO machine translation of FR 2735369, http://worldwide.espacenet.com/, accessed online on Jan. 20, 2016.*
Ruiz-Capillas et al., Flow Injection Analysis of Food Additives, Dec. 1, 2015, CRC Press, p. 225-228 and 238.*
Heyneman et al., Drugs, 2000, 60(3), p. 555-574.*
Arvind, et al., "Simultaneous estimation of thioclochicoside and diclofenac potassium by UV spectometer using multicomponent method", International Journal of Chemtech Research, vol. 3, No. 2, Apr. 1, 2011, pp. 944-945.
International Search Report and Written Opinion of PCT/EP2013/071925 of Jan. 7, 2014.
International Preliminary Report on Patentability of PCT/EP2013/071925 of Nov. 11, 2014.

* cited by examiner

*Primary Examiner* — Jonathan S Lau
(74) *Attorney, Agent, or Firm* — Silvia Salvadori, P.C.; Silvia Salvadori

(57) ABSTRACT

The invention relates to a stable injectable aqueous solution containing diclofenac and thiocolchicoside, or pharmaceutically acceptable salts thereof, and the use thereof in the treatment of painful and inflammatory rheumatic or traumatic conditions of the joints, muscles, tendons and ligaments.

12 Claims, No Drawings

STABLE INJECTABLE COMPOSITION CONTAINING DICLOFENAC AND THIOCOLCHICOSIDE

This application is a U.S. national stage of PCT/EP2013/071925 filed on 21 Oct. 2013, which claims priority to and the benefit of Italian Application No. MI2012a001782 filed on 22 Oct. 2012, the contents of which are incorporated herein by reference in their entireties.

The present invention relates to a stable injectable composition containing diclofenac and thiocolchicoside, or pharmaceutically acceptable salts thereof, and its use in the treatment of painful and inflammatory rheumatic or traumatic conditions of the joints, muscles, tendons and ligaments.

BACKGROUND TO THE INVENTION

Diclofenac (2-(2-[2,6-dichlorophenylamino]phenyl)acetic acid) is one of the most widely used non-steroidal anti-inflammatory drugs due to its marked pharmacological activity.

A number of formulations of diclofenac for parenteral administration are known, wherein it is present, for example, as a sodium, potassium, diethylamine or 2-hydroxyethylpyrrolidine salt.

Parenteral formulations of diclofenac, in particular of its sodium salt, are disclosed, for example, in U.S. Pat. No. 4,711,906.

Thiocolchicoside, also known as 3-demethyl-thiocolchicine glucoside, is a glucoside extracted from the seeds of *Colchicum autumnale*, which possesses a muscle-relaxant, anti-inflammatory, analgesic and anaesthetic action. It is frequently administered in combination with other medicaments, such as anti-inflammatories.

Patent application PCT/TR2009/000137 discloses pharmaceutical compositions containing thiocolchicoside and a non-steroidal anti-inflammatory drug. The compositions can take the form of an aqueous or non-aqueous solution suitable for intravenous, intramuscular or subcutaneous injection.

Pharmaceutical compositions in solid form containing a diclofenac salt and thiocolchicoside are disclosed in EP 0837684A1 (equivalent to FR2735369).

Patent application PCT/EP2012/061468 discloses a patch for transdermal release, containing diclofenac or a pharmaceutically acceptable salt thereof and thiocolchicoside.

WO2012/053012 discloses a topical composition in the form of a nanoemulsion comprising diclofenac sodium salt and thiocolchicoside.

Pharmaceutical compositions containing 25 or 75 mg of diclofenac sodium salt and 2 or 4 mg of thiocolchicoside in the form of an injectable solution are described in Minerva Anestesiologica, October 1991, pages 1084-1085 and in Bollettino Chimico Farmaceutico 1993, 132/6, pages 203-209. They are a combination of two separate preparations of diclofenac and thiocolchicoside useful for extemporaneous administration. Said extemporaneous injectable solutions are not proprietary medicaments properly so called, as in practice they are prepared at the time of use, and consequently lack long-term stability data.

The availability of a novel association between diclofenac and thiocolchicoside simultaneously present in a pharmaceutical form which presents as a stable injectable preparation in the terms required by the health authorities is therefore of great interest.

The prior art demonstrates that diclofenac is a substance which is relatively unstable in solution, and that the liquid formulations of said substance therefore require the presence of a stabilising agent. The above-mentioned U.S. Pat. No. 4,711,906 discloses stable aqueous solutions of diclofenac containing a mixture of propylene glycol and polyethylene glycol. The chemical stability of said solutions is obtained by adding a reducing agent which can be a sulphite, such as sodium bisulphite, cysteine and/or cysteine hydrochloride, acetylcysteine and/or acetylcysteine hydrochloride, or a thiosulphate. Their chemical stability is further improved by the presence of lidocaine in addition to the reducing agent.

When preparing a liquid composition containing diclofenac and thiocolchicoside, the inventors of the present application have found that it is necessary to overcome a number of technological difficulties, the most important requirement being to prevent the degradation of one or both of the active ingredients when formulated in a single unit dose solution.

The antioxidant most widely used to stabilise diclofenac in liquid solutions is sodium bisulphite. There are numerous formulations on the market containing this antioxidant. Other antioxidants used are cysteine, acetylcysteine and reduced glutathione.

Thiocolchicoside also presents stability problems in solution. The chemical and physical compatibility of thiocolchicoside with other injectable medicaments frequently combined with it, including anti-inflammatories, is described in Farmaco, 2002, 57(11), 925-930.

The authors of the present invention have found that the addition of thiocolchicoside to a formulation containing diclofenac makes the use of the above-mentioned antioxidants problematic, if not impossible, as their presence in the solution causes significant degradation of thiocolchicoside and diclofenac under ambient and supra-ambient storage conditions (40° C.). As the number of antioxidants suitable for parenteral/injectable use is limited, the impossibility of using said stabilizing agents makes it very complex to obtain formulations which are potentially stable under the conditions required by the health authorities when the product is registered.

Tert-butyl-4-hydroxyanisole, also known as butylated hydroxyanisole or BHA, is an antioxidant widely used in the food and pharmaceutical industry. It is used in fats and oils, foods containing fats, essential oils, and food packaging materials. BHA is a mixture of two isomers: 2-tert-butyl-4-hydroxyanisole (2-BHA) and 3-tert-butyl-4-hydroxyanisole (3-BHA). The two BHA isomers are phenols and therefore react rapidly with free radicals, thus protecting the foods to which they are added against oxidation and alteration of their organoleptic characteristics (colour, odour, flavour and texture).

DESCRIPTION OF THE INVENTION

The object of the present invention is a stable pharmaceutical composition in the form of an injectable aqueous solution containing diclofenac and thiocolchicoside or a pharmaceutically acceptable salt thereof. The present invention solves the technical problem of the instability of liquid formulations containing a combination of diclofenac and thiocolchicoside.

DETAILED DESCRIPTION OF THE INVENTION

The composition of the invention contains tert-butyl 4-hydroxyanisole (BHA) as antioxidant.

Diclofenac is preferably present in the composition as sodium, potassium, calcium or ammonium salt. Diclofenac sodium salt is particularly preferred.

The composition of the invention can optionally also contain excipients suitable for pharmaceutical use, such as mannitol and sorbitol, and can also contain a local anaesthetic, such as lidocaine.

mg, and thiocolchicoside at the concentration of 1 mg/mL, corresponding to a dosage unit amount of 4 mg.

The data set out in Table 1 prove the stability of a composition according to the invention containing diclofenac sodium salt, thiocolchicoside and BHA, compared with the same composition wherein BHA is replaced by the antioxidant sodium metabisulphite or N-acetylcysteine. Stability was monitored by HPLC analysis.

TABLE 1

| | | | | | | |
|---|---|---|---|---|---|---|
| Antioxidant in formula: Sodium metabisulphite | | | | | | |
| Time/Storage | Batch | Thiocol. content (%) | Diclof. content (%) | Thiocol. impurity (RRT = 0.49.%) | Thiocol. impurity (RRT = 0.54.%) | Thiocol. impurity (RRT = 0.64.%) |
| 1 month/40° C. | TFR12074B | 89.8 | 93.6 | 2.93 | 0.33 | NA |
| Antioxidant in formula: N-acetylcysteine | | | | | | |
| Time/Storage/ Concentration | Batch | Thiocol. content (%) | Diclof. content (%) | Thiocol. impurity (RRT = 0.49.%) | Thiocol. impurity (RRT = 0.54.%) | Thiocol. impurity (RRT = 0.64.%) |
| 1 day/Ambient Temperature @ 0.5 mg mL$^{-1}$ | TFR12195A | 86.3 | NA | NA | 0.28 | 0.06 |
| 1 day/Ambient Temperature @ 30 mg mL$^{-1}$ | TFR12195B | 11.8 | NA | 69.50 | 0.33 | 1.04 |
| Antioxidant in formula: Butylated hydroxyanisole (BHA) | | | | | | |
| Time/Storage | Batch | Thiocol. content (%) | Diclof. content (%) | Thiocol. impurity (RRT = 0.49.%) | Thiocol. impurity (RRT = 0.54.%) | Thiocol. impurity (RRT = 0.64.%) |
| 1 month/40° C. | TFR12189A | 99.25 | 98.27 | ND | 0.61 | ND |

NA = Not Analysed
ND = Not Detectable
RRT = Relative Retention Time

The composition according to the invention can also contain solubilising agents, chelating agents, buffering agents or pH correctors, such as sodium or potassium hydroxide, sodium bicarbonate, tromethamine, monoethanolamine or other organic bases.

In one embodiment of the invention the composition takes the form of an aqueous solution consisting of a mixture of water and propylene glycol.

In a preferred embodiment of the invention the composition takes the form of an aqueous solution containing propylene glycol and diclofenac sodium salt.

Diclofenac sodium salt is preferably present in the composition in quantities ranging from 25 to 75 mg per unit dose administered.

Thiocolchicoside can be present in the composition in quantities ranging from 1 to 10 mg per unit dose administered.

BHA can be present in the composition in quantities ranging from 0.1 to 1.2 mg per unit dose administered.

The excipients mannitol or sorbitol can be present in the composition in quantities ranging from 6 to 32 mg per unit dose administered.

Propylene glycol can be present in the composition in quantities ranging from 800 to 2000 mg per dosage unit.

In a preferred embodiment of the invention the composition contains diclofenac sodium salt at the concentration of 18.75 mg/mL, corresponding to a dosage unit amount of 75

It will be observed that the presence of sodium metabisulphite or N-acetylcysteine causes the degradation of thiocolchicoside and, in the presence of sodium metabisulphite, which is the preferred antioxidant for injectable diclofenac, also of the latter active ingredient. Degradation is observed both under ambient storage conditions and at 40° C.

Conversely, the use of BHA enables the composition to maintain thiocolchicoside and diclofenac contents exceeding 99% and 98% respectively, even after one month's storage at 40° C. Moreover, under these storage conditions two of the three impurities typically associated with the degradation of thiocolchicoside in solution are undetectable.

It has also surprisingly been found that the use of BHT (butylated hydroxytoluene, 2,6-bis(1,1-dimethylethyl)-4-methylphenol), an antioxidant which also has a phenol structure and is a close analogue of BHA, is unsuitable to guarantee the stability of a solution of diclofenac and thiocolchicoside, as it is associated with problems of poor solubility and precipitation under ordinary storage conditions.

The injectable composition according to the invention is suitable for intravenous, intramuscular or subcutaneous administration, and can be prepared by conventional methods well-known to the skilled person.

By way of example, Table 2 below shows the quantitative composition of a dosage unit (4 mL vial) according to the invention.

TABLE 2

| Ingredient | mg |
|---|---|
| Diclofenac sodium salt | 75 |
| Thiocolchicoside | 4 |
| Mannitol | 6 |
| Tert-butylhydroxyanisole | 0.2 |
| Propylene glycol | 1600 |
| Sodium hydroxide | q.s. for pH 8.0-8.5 |
| Purified water | q.s. for 4 mL |

The composition reported in Table 2 represents a particularly preferred embodiment of the invention.

A further aspect of the invention relates to the use of the composition according to the invention for the treatment of rheumatic or traumatic pain and inflammation of the joints, muscles, tendons and ligaments, in particular for the treatment of articular and extra-articular inflammatory rheumatological disorders, acute and chronic lumbosciatalgia, cervical neuralgia, torticollis and painful post-traumatic and post-operative syndromes.

The composition according to the invention can be administered in dosage unit amounts of 75 mg of diclofenac sodium and 4 mg of thiocolchicoside once or twice a day.

The invention will now be illustrated by the following example.

Preparation of 1037.5 mL of Injectable Solution of Diclofenac Sodium Salt and Thiocolchicoside, Corresponding to 250 Vials Preparation of the Bulk Solution According to the procedures the requested amount of Propylene Glycol (415 g) is poured into the dissolution tank, the stirring system is switched on and the component is heated up to 40±5° C. The amount of Butylhydroxyanisole, 51.9 mg, is introduced into the dissolution tank and the preparation is stirred for 20±10 minutes or until complete dissolution. Switch off the stirring system and verify the appearance of the solution: clear and colourless. Cool down to 25±5° C., switch on the stirring system, then add the requested amount of water for injection (636.61 g) and Mannitol (1.6 g), then stir for 15±5 minutes. Switch off the stirring system and verify the appearance of the solution: clear and colourless.

Switch on the stirring system, then load Diclofenac Sodium (19.5 g) and stir for 40±10 minutes or until complete dissolution. Switch off the stirring system and verify the appearance of the solution: clear and colourless.

Switch on the stirring system, then load Thiocolchicoside (1.0375 g) and mix for 20±5 minutes or until complete dissolution. Switch off the stirring system and verify the appearance of the solution: clear yellow to amber solution.

Carry out the check of the density value (1.020-1.050 g/mL) and if necessary bring to weight with distilled water, then stir for about 10 minutes, switch off the stirring system and check again the appearance of the solution: clear yellow to amber solution.

Verify the pH Value (7.0-9.0).

Filtration of the Solution

The prepared solution is conveyed through a 0.22 µm disposable filter cartridge, from the dissolution vessel to a sterile stainless steel container. Keep the tank under $N_2$ pressure. Filter the solution, check the integrity of the filter before and after the filtration.

Filling of the Ampoules

The ampoules to be filled are previously depyrogenated and introduced in the filling room according to standard operating procedures. Equipment and filling parts are also cleaned and sterilized prior to use. Aseptic filling occurs in grade A environment with grade B background.

The tank, under $N_2$ pressure, filled up during step 3, is connected to the ampoule filling machine. The solution immediately prior to filling undergoes to a further 0.22 µm sterile filtration (Membrane: Nylon 6,6, covalently-modified positive Zeta/Housing: Polypropylene). After the assembling of syringes, pistons, needles, tubes and filter, all the circuit is flushed with the solution to be filled and the desired volume (filling volume 4.15 ml*) is adjusted. The filling procedure starts and the ampoules are filled, hermetically sealed by fusion of the glass and collected in the steel trays. Before and at the end of the filling, check the integrity of the 0.22 µm sterile filter. The sealed ampoules are tested for integrity at the end of filling step.

* An overfill of 0.15 mL is applied to guarantee the minimum extractable volume of 4.0 mL.

The invention claimed is:

1. Pharmaceutical composition in the form of an injectable aqueous solution comprising diclofenac and thiocolchicoside or a pharmaceutically acceptable salt thereof as the active ingredients and tert-butylhydroxyanisole as stabilizer, wherein the composition does not comprise sodium metabisulphite and/or N-acetylcysteine.

2. Composition according to claim 1, comprising diclofenac sodium salt.

3. Composition according to claim 1, wherein said aqueous solution comprises a mixture of water and propylene glycol.

4. Composition according to claim 1, further comprising an additional ingredient selected from local anaesthetic, solubilising agent, chelating agent, buffering agent and pH corrector.

5. Composition according to claim 1, comprising diclofenac sodium salt in amounts ranging from 25 to 75 mg per dosage unit.

6. Composition according to claim 5, wherein said amount is 75 mg.

7. Composition according to claim 1, comprising thiocolchicoside in amounts ranging from 1 to 10 mg per dosage unit.

8. Composition according to claim 7, wherein said amount is 4 mg.

9. Composition according to claim 1, comprising tert-butylhydroxyanisole in amounts ranging from 0.1 to 1.2 mg per dosage unit.

10. Composition according to claim 9, wherein said amount is 0.2 mg.

11. Composition according to claim 1, consisting of the following ingredients and amounts per dosage unit:

| Ingredient | mg |
|---|---|
| Diclofenac sodium salt | 75 |
| Thiocolchicoside | 4 |
| Mannitol | 6 |
| tert-butylhydroxyanisole | 0.2 |
| Propylene glycol | 1600 |
| Sodium hydroxide | q.s. for pH 8.0-8.5 |
| Purified water | q.s. for 4 mL |

12. Method of treatment of joint, muscle, tendon or ligament pain and inflammation of rheumatic or traumatic origin, said method comprising:
    administering an effective amount of the composition of claim 1 to a subject in need thereof; and
    treating said joint, muscle, tendon or ligament pain and inflammation of rheumatic or traumatic origin.

* * * * *